(12) United States Patent
Boomgaarden et al.

(10) Patent No.: US 7,954,996 B2
(45) Date of Patent: Jun. 7, 2011

(54) POSITIONING SYSTEM WITH TILTING ARM SUPPORT FOR IMAGING DEVICES

(75) Inventors: Jonathan Boomgaarden, Waukesha, WI (US); Matthew Aaron Halsmer, Westfield, IN (US)

(73) Assignee: General Electric Company, Schenectady, NY (US)

( * ) Notice: Subject to any disclaimer, the term of this patent is extended or adjusted under 35 U.S.C. 154(b) by 198 days.

(21) Appl. No.: 12/169,525

(22) Filed: Jul. 8, 2008

(65) Prior Publication Data

US 2010/0006727 A1   Jan. 14, 2010

(51) Int. Cl.
*G03B 42/04* (2006.01)
*H01J 31/49* (2006.01)

(52) U.S. Cl. .................... 378/189; 378/167

(58) Field of Classification Search ............. 378/167, 378/182, 189, 190, 193, 196–198
See application file for complete search history.

(56) References Cited

U.S. PATENT DOCUMENTS

| | | | | |
|---|---|---|---|---|
| 2,965,758 | A | * | 12/1960 | Malick .................... 378/58 |
| 3,784,837 | A | * | 1/1974 | Holmstrom ............... 378/189 |
| 4,233,516 | A | * | 11/1980 | Trepte .................... 378/181 |
| 4,365,344 | A | * | 12/1982 | Dornheim ................. 378/189 |
| 4,426,725 | A | * | 1/1984 | Grady .................... 378/196 |
| 4,501,011 | A | * | 2/1985 | Hauck et al. ............. 378/196 |
| 4,625,731 | A | | 12/1986 | Quedens et al. |
| 4,912,754 | A | | 3/1990 | Van Steenburg |
| 4,991,441 | A | | 2/1991 | Nottingham et al. |
| 5,042,487 | A | | 8/1991 | Marquardt |
| 5,048,071 | A | | 9/1991 | Van Steenburg |
| 5,067,145 | A | * | 11/1991 | Siczek et al. ............. 378/198 |
| 5,096,291 | A | | 3/1992 | Scott |
| 5,127,032 | A | | 6/1992 | Lam et al. |
| 5,157,707 | A | * | 10/1992 | Ohlson ................... 378/181 |
| 5,386,447 | A | | 1/1995 | Siczek |
| 5,547,453 | A | | 8/1996 | Di Perna |
| 5,572,569 | A | | 11/1996 | Benoit et al. |
| 5,658,238 | A | | 8/1997 | Suzuki et al. |
| 5,799,054 | A | | 8/1998 | Hum et al. |
| RE36,415 | E | | 11/1999 | McKenna |
| 6,007,243 | A | * | 12/1999 | Ergun et al. .............. 378/197 |
| 6,027,247 | A | | 2/2000 | Tachi et al. |
| 6,097,030 | A | | 8/2000 | Tokarski et al. |
| 6,234,672 | B1 | * | 5/2001 | Tomasetti et al. ........... 378/197 |
| 6,317,618 | B1 | | 11/2001 | Livni et al. |
| 6,325,537 | B1 | * | 12/2001 | Watanabe ................ 378/197 |
| 6,414,490 | B1 | | 7/2002 | Damadian et al. |
| 6,434,329 | B1 | | 8/2002 | Dube et al. |
| 6,504,371 | B1 | | 1/2003 | Damadian et al. |
| 6,640,363 | B1 | | 11/2003 | Pattee et al. |
| 6,642,686 | B1 | | 11/2003 | Ruch |
| 6,702,372 | B2 | | 3/2004 | Tholkes et al. |
| 6,773,161 | B2 | * | 8/2004 | Tanaka ................... 378/198 |
| 6,847,336 | B1 | | 1/2005 | Lemelson et al. |
| 6,851,851 | B2 | * | 2/2005 | Smith et al. .............. 378/189 |
| 6,906,328 | B2 | | 6/2005 | Garrard et al. |
| 6,979,123 | B2 | * | 12/2005 | Barta et al. .............. 378/197 |
| 7,108,421 | B2 | | 9/2006 | Gregerson et al. |

(Continued)

*Primary Examiner* — Edward J Glick
*Assistant Examiner* — Thomas R Artman
(74) *Attorney, Agent, or Firm* — Dean Small; The Small Patent Law Group (57) ABSTRACT

A positioning system for imaging devices is provided. The positioning system includes an imaging element and a tilting arm support having the imaging element coupled thereto. The tilting arm support includes a linkage to tilt the imaging element when the tilting arm support moves.

21 Claims, 9 Drawing Sheets

U.S. PATENT DOCUMENTS

| | | |
|---|---|---|
| 7,152,261 B2 | 12/2006 | Jackson |
| 7,188,998 B2 | 3/2007 | Gregerson et al. |
| 7,418,080 B2 * | 8/2008 | Fadler ............................ 378/65 |
| 7,517,149 B2 * | 4/2009 | Agrawal et al. ............... 378/198 |
| 7,540,659 B1 * | 6/2009 | Halsmer et al. ............... 378/189 |
| 7,566,170 B2 * | 7/2009 | Halsmer et al. ............... 378/189 |
| 2004/0172012 A1 | 9/2004 | Otsuka et al. |
| 2006/0050843 A1 | 3/2006 | Strommer et al. |
| 2006/0185090 A1 | 8/2006 | Jackson |
| 2006/0256921 A1 | 11/2006 | Tachibana et al. |
| 2007/0003021 A1 | 1/2007 | Guertin et al. |
| 2007/0010801 A1 | 1/2007 | Chen et al. |
| 2007/0107128 A1 | 5/2007 | Somasundaram et al. |
| 2007/0169265 A1 | 7/2007 | Saracen et al. |
| 2009/0279671 A1 * | 11/2009 | Zhang .......................... 378/167 |

* cited by examiner

POSITIONING SYSTEM WITH TILTING ARM SUPPORT FOR IMAGING DEVICES

BACKGROUND OF THE INVENTION

This invention relates generally to positioning systems, and more particularly to positioning systems that allow movement and tilting of an imaging device.

Imaging devices, such as diagnostic imaging devices, are often mounted to a support that allows positioning of the imaging device at different positions and orientations. These supports may allow height adjustments as well as tilting or rotational adjustments. For example, in x-ray diagnostic medical imaging systems, such as a wall-stand radiographic imaging systems, the support mechanism for the imaging portion of the systems typically allow placement of the imaging portion in different imaging positions. The imaging portion may be positioned, for example, in a vertical or upright position to perform, for example, a standing chest exam and in a horizontal position to perform, for example, a table exam (e.g., x-ray of a patient lying on a stretcher) or a sitting patient exam (e.g., x-ray of a leg of a patient in a wheelchair).

In these conventional positioning systems, the pivot point is located at a position along a back surface of a receptor that receives the imaging portion such that the receptor elevates when a support of the positioning system is extended. Thereafter, pivoting the imaging portion from a vertical position to horizontal position at this higher elevation can make it more difficult and painful to perform a sitting patient exam (due to having to raise the patient's leg higher). Moreover, the system may not allow extension far enough outward from a wall to perform a table exam. As a result, different positioning systems having different supports and stands (e.g., wall stands) are used, such as a general purpose system for standing exams and a long arm system for table exams. Also, in these known systems, because of the movement of the center or gravity during position changes of the imaging portion, a large counter balance or weight is often needed. It is also important that these positioning systems minimize the space needed in the room when the imaging component is in the vertical position while positioning the imaging component close to the floor when in the horizontal position.

BRIEF DESCRIPTION OF THE INVENTION

In one embodiment of the invention, a positioning system is provided that includes an imaging element and a tilting arm support having the imaging element coupled thereto. The tilting arm support includes a linkage to tilt the imaging element when the tilting arm support moves.

In another embodiment of the invention, a tilting arm support for supporting an imaging element is provided that includes a first sprocket and a second sprocket. The tilting arm support further includes a linkage coupling the first sprocket and the second sprocket to tilt the imaging element when the first and second sprockets rotate. A center of gravity of the imaging element remains substantially vertically constant when the imaging element rotates between a vertical position and a horizontal position as the first and second sprockets rotate.

In yet another embodiment of the invention, a method for positioning an imaging element is provided. The method includes coupling a first sprocket to a second sprocket and configuring a tilting arm support to pivot an imaging element when the first and second sprockets rotate to move the tilting arm support.

DETAILED DESCRIPTION OF THE INVENTION

As used herein, an element or step recited in the singular and proceeded with the word "a" or "an" should be understood as not excluding plural of said elements or steps, unless such exclusion is explicitly stated. "Patient" and "individual," as used herein, may include not only humans but also animals. Furthermore, references to "one embodiment" of the present invention are not intended to be interpreted as excluding the existence of additional embodiments that also incorporate the recited features. Moreover, unless explicitly stated to the contrary, embodiments "comprising" or "having" or "including" an element or a plurality of elements having a particular property may include additional such elements not having that property.

Various embodiments provide a positioning system including a tilting arm support having a geared linkage having a single degree of freedom. The tilting arm support creates a virtual pivot point such that an imaging element at an end of the tilting arm support tilts at the same time the tilting arm support is extended. At least one technical effect of the various embodiments is that the center of gravity of the tilting arm support does not change vertically as the position of the arm is changed such that the net effect of gravity on the arm is removed and only frictional forces are present when moving the imaging element at the end of the arm between vertical and horizontal positions. The various embodiments also allow an imaging element to maintain a low position when extended relative to the initial height of the arm.

It should be noted that although the various embodiments described herein are described in connection with supporting and positioning a diagnostic imaging element, the various embodiments are not limited to diagnostic imaging applications or to imaging applications. For example, the various embodiments may be implemented in connection with non-destructive imaging systems or in general for supporting a load at an end of an arm, wherein the load rotates between a vertical and horizontal position as the load is moved away from or toward a support, or vice versa.

Figure 1:
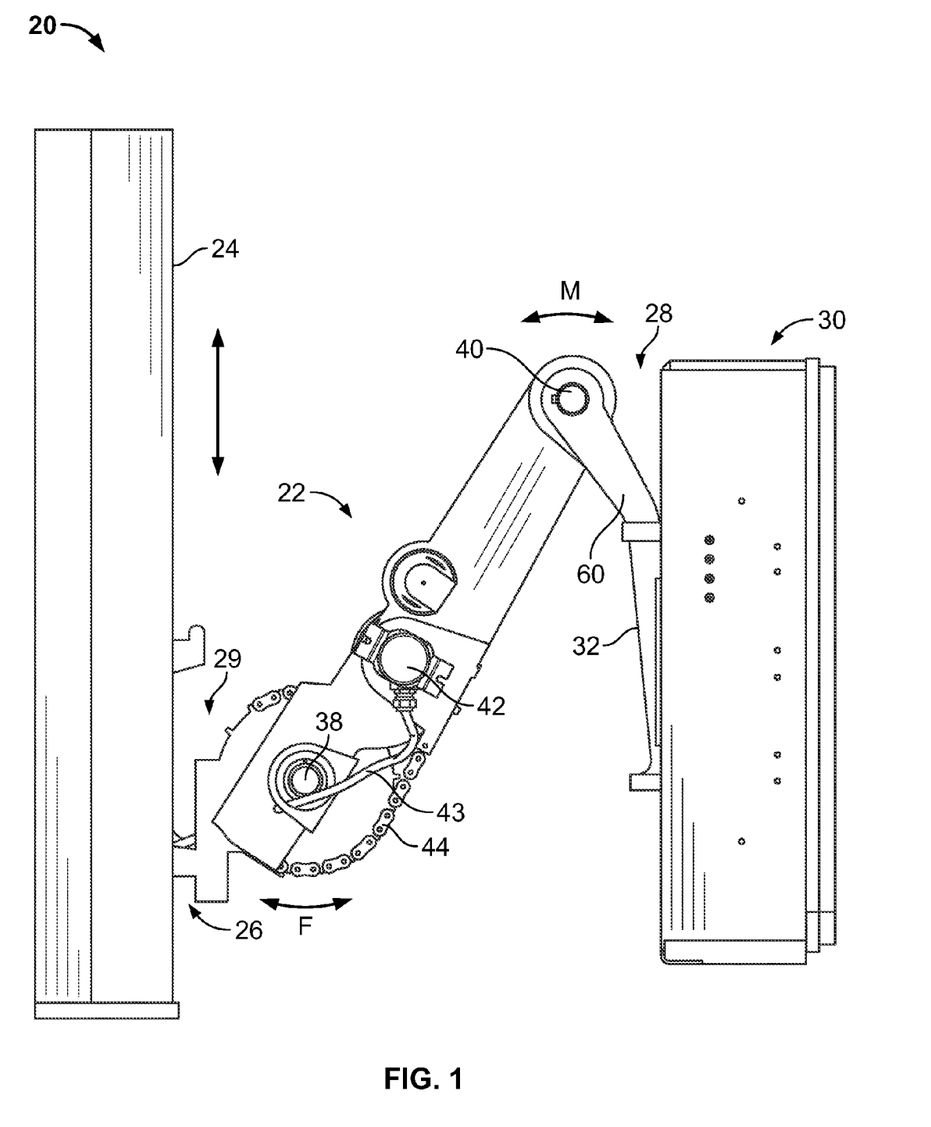
FIG. 1 is a side elevation view of a positioning system with a tilting arm support formed in accordance with various embodiments of the invention.

Specifically, as shown in FIG. 1, which is a side elevation view of a positioning system 20 formed in accordance with various embodiments of the invention, the positioning system 20 includes a tilting arm support 22 that is mounted to a vertical support 24. The vertical support may be a wall stand or similar structure. For example, in one embodiment, the vertical support 24 is an x-ray wall stand for use with an analog x-ray system (e.g., the GE Healthcare Silhouette VR analog x-ray system) or a digital radiographic system (e.g., the GE Healthcare Definium 5000 digital radiographic system).

Figure 2:
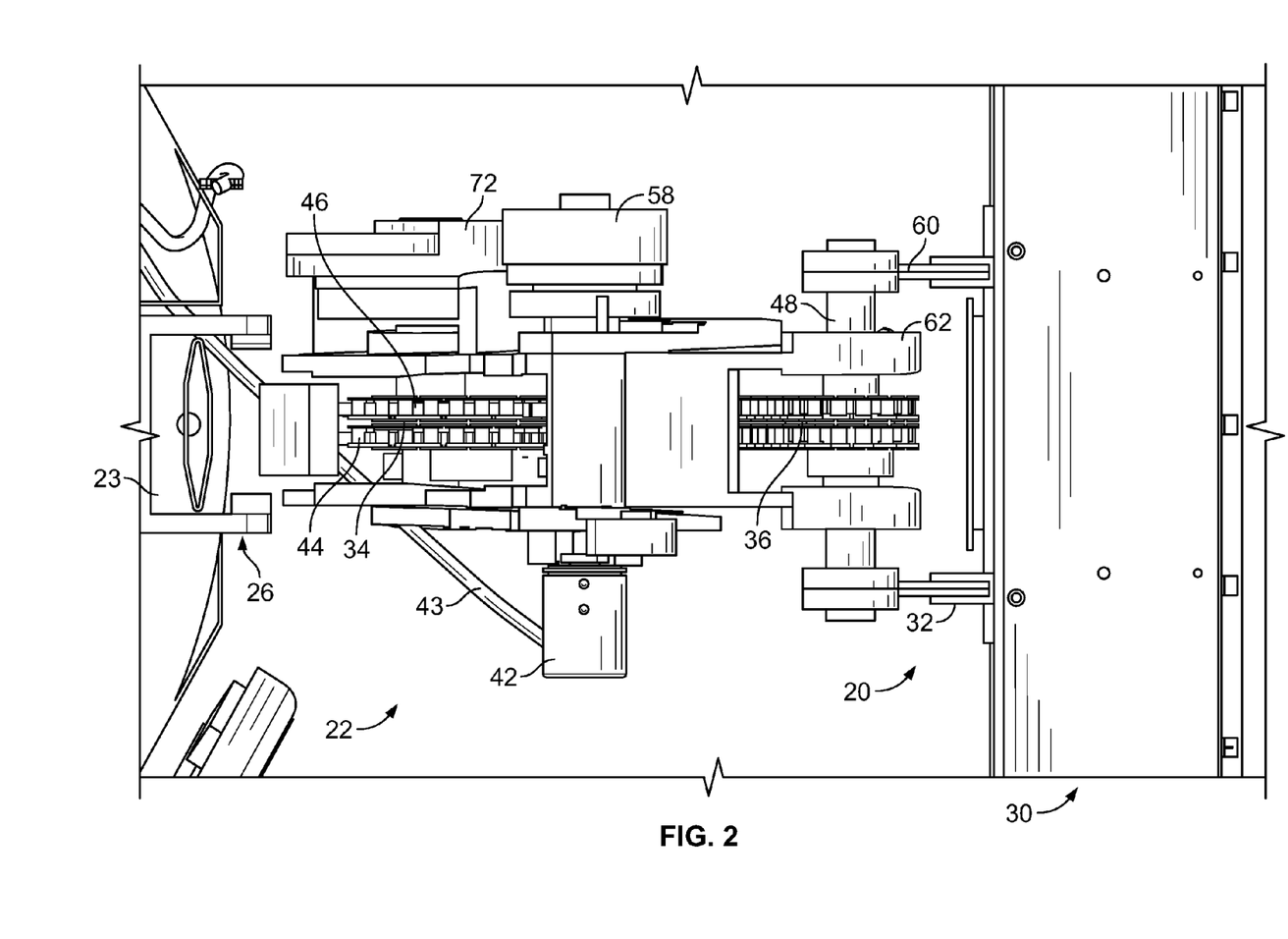
FIG. 2 is a top plan view of the positioning system of FIG. 1.

The tilting arm support 22 is mounted to the vertical support 24 using a mounting member 26 that is slidingly engaged with the vertical support 24 as is known such that the tilting arm support 22 can translate vertically upward and downward along the vertical support 24 (as illustrated by the arrow). The mounting member 26 also allows locking of the tilting arm support 22 at any horizontal position along the vertical support 24, for example, along a channel 23 (shown in FIG. 2) of the vertical support 24.

Figure 3:
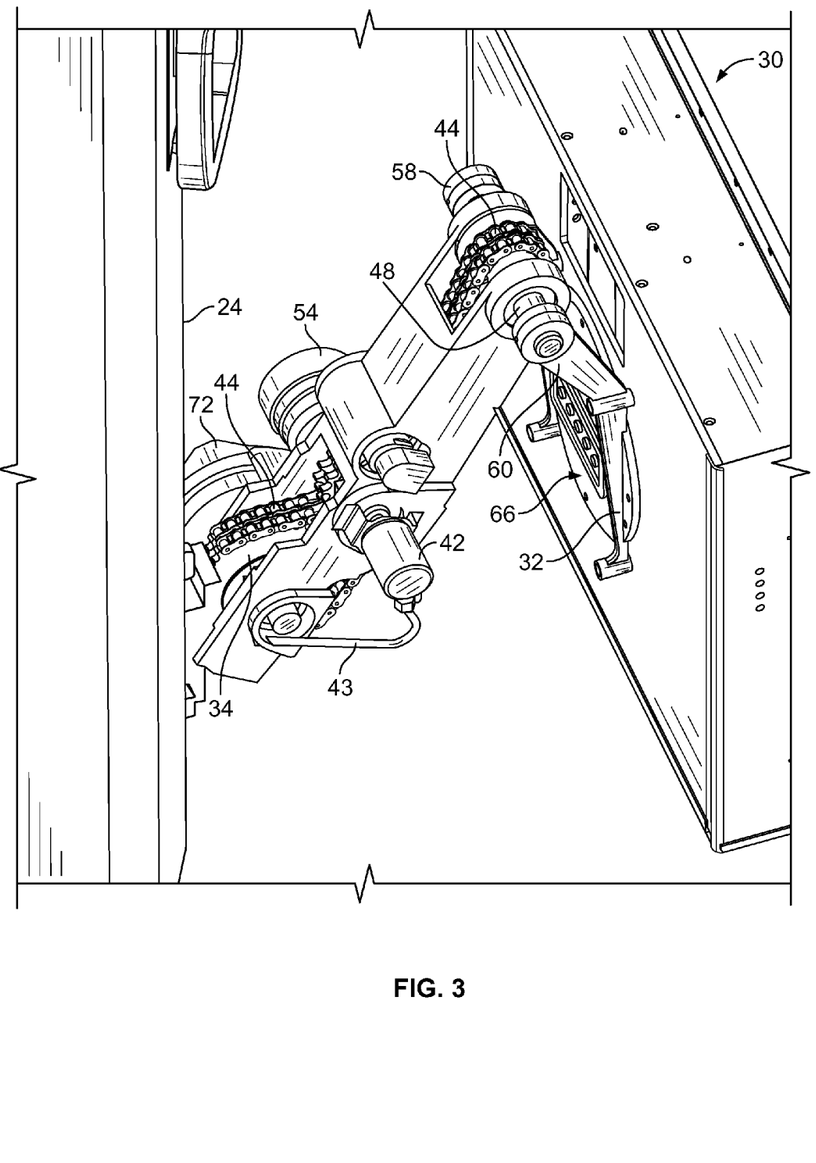
FIG. 3 is a perspective view of the positioning system of FIG. 1 showing attachment of the tilting arm support to an imaging element.
Figure 4:
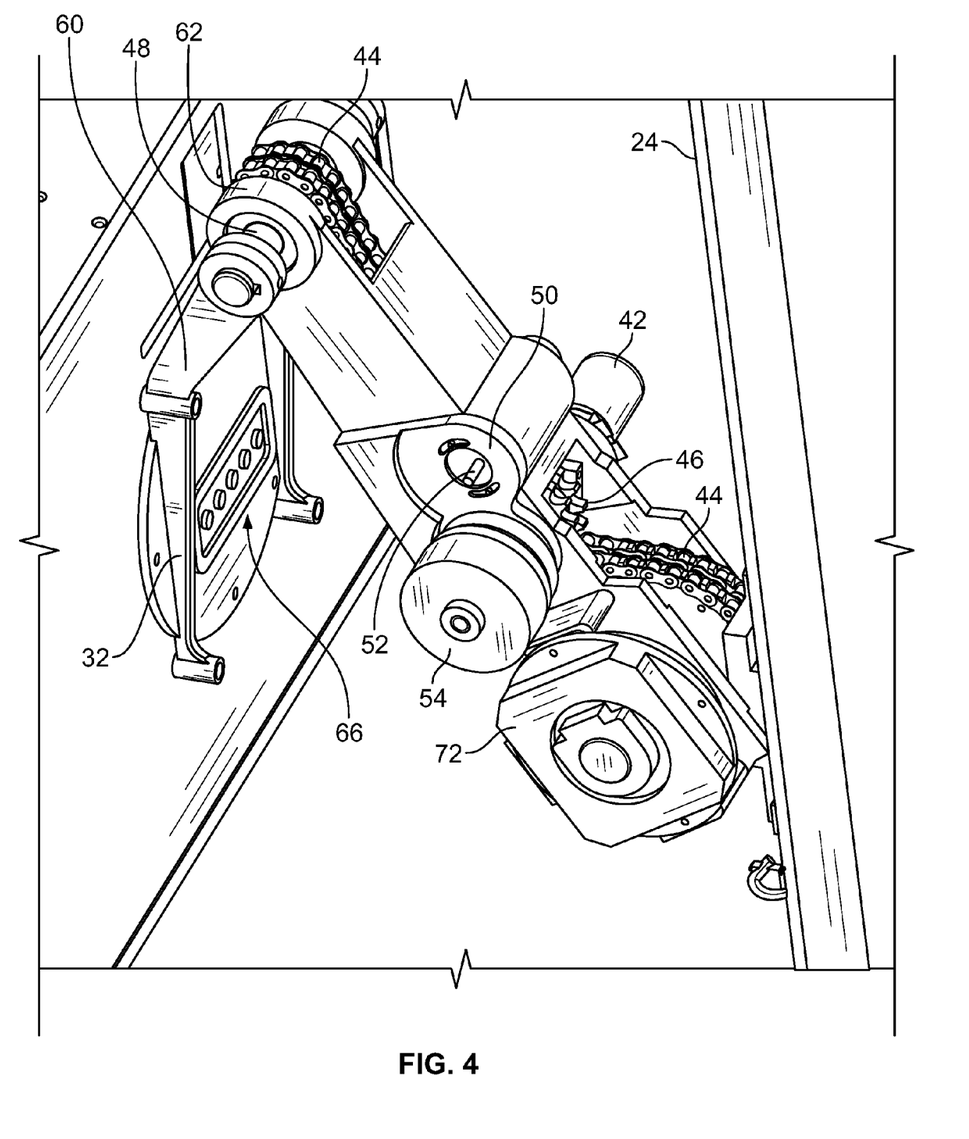
FIG. 4 is an enlarged perspective view of the positioning system of FIG. 1 showing attachment of the tilting arm support to an imaging element.

The tilting arm support 22 includes at an end 28, which is opposite an end 29 where the tilting arm support 22 is mounted to the vertical support 24, an imaging element 30, for example an x-ray detector mounted thereto. The imaging element 30 may be of any shape (illustrated as generally rectangular) and includes on a front surface an image receptor or digital film as is known. The imaging element 30 may be any type of imaging component or device. The imaging element 30 is coupled to the end 28 of the tilting arm support 22 using a bracket 32 or similar mounting device as shown more clearly in FIGS. 3 and 4. The tilting arm support 22 generally defines an extending arm structure that includes a first sprocket 34 and a second sprocket 36 (as shown more clearly in FIG. 5) that define a first fixed pivot point 38 (illustrated by the arrow F) and a second moving pivot point 40 (illustrated by the arrow M), respectively. The first sprocket 34 is located at the end 29 of the tilting arm support 22 adjacent the vertical support 24 and the second sprocket 36 is located at the end 28 of the tilting arm support 22 adjacent the imaging element 30.

An encoder 42 is mounted to the tilting arm support 22 to provide position information as feedback for controlling the movement of the tilting arm support 22. Feedback information may be communicated through communication lines 43, which are shown encased within a protective covering, such as a sheath. As shown more clearly in FIGS. 2 and 5, one or more chains 44 (a double roller chain is shown) defines a linkage that couples the first sprocket 34 and the second sprocket 36 via an intermediate sprocket 46 (shown in FIG. 5). The first sprocket 34 is mounted to a shaft 47 (shown in FIG. 5) and the second sprocket 36 is mounted to a shaft 48 to allow relative movement therebetween. It should be noted that the linkage may be any type of linked connection and the various embodiments are not limited to a chain linkage. For example, instead of or in addition to a chain, such as a roller chain, a belt, a band or any other mechanical linkage may be provided.

Figure 5:
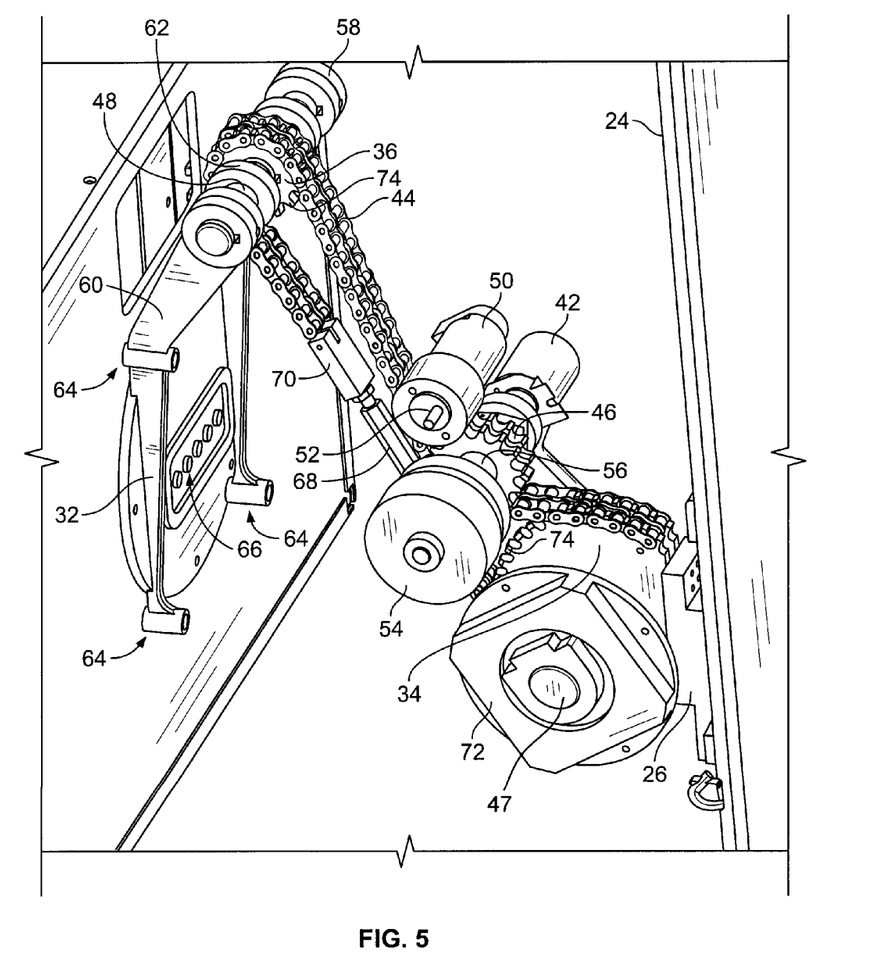
FIG. 5 is a perspective view of the positioning system of FIG. 1 with covers removed to show sprockets and a linkage of various embodiments of the invention.

A motor 50, as shown more clearly in FIG. 5 (where covers of the tilting arm support 22 are removed) includes a shaft 52 extending therefrom that drives the intermediate sprocket 46 using a clutch 54 mounted to a shaft 56 on which the intermediate sprocket 46 is coupled and rotates. The shaft 56 of the motor 50 is coupled to the clutch 54 using, for example, a timing belt and pulley arrangement (not shown) that can be implemented in any known manner.

A tensioner 58 is connected to the shaft 48 to adjust the pivoting tension of the second sprocket 36 relative to the imaging element 30. The imaging element 30 is coupled to the second sprocket 36 via arms 60 of the bracket 32 that are held in place by a guide member 62. The imaging element 30 is connected to the bracket 32 at one or more connection points 64 using, for example, a bolt that extends through portions of the bracket 32 at the connection points 64. The arms 60 are slightly angled or curved to provide a fixed orientation of the imaging element 30 relative to the tilting arm support 22 and that also allows the imaging element 30 to rotate slightly past either vertical or horizontal as described in more detail below. The imaging element 30 may include input controls 66 for controlling the operation of the imaging element 30 as is known.

Referring specifically to FIG. 5, the one or more chains 44 form a single moving structure. In particular, each end of the one or more chains 44 is connected to the opposite end of the one or more chains 44 using a turn buckle 68 coupled to a block 70 (only one shown) at each end of the one or more chains 44. Also, the position of the one or more chains 44 may be locked using a locking member 72, which is connected to the first sprocket 34 and that can lock the first sprocket 34 to prevent movement thereof.

In the various embodiments, the one or more chains 44 engage the first and second sprockets 34 and 36 such that movement of the one more chains 44 by the intermediate sprocket 46 driven by the motor 50 causes the first and second sprockets 34 and 36 to rotate in the same direction, for example, both rotate in a clockwise direction or a counter-clockwise direction. Accordingly, the first and second sprockets 34 and 36 pivot in the same direction causing the imaging element 30 to pivot upward as the tilting arm support 22 is extended outward (away from the vertical support 24) to rotate the imaging element 30 from a generally vertical position to a generally horizontal position and to pivot downward as the tilting arm support 22 is retracted inward (toward the vertical support 24) to rotate the imaging element 30 from a generally horizontal position to a generally vertical position. In this embodiment, the one or more chains 44 extend over and around the first and second sprockets 34 and 36, and under the intermediate sprocket 46.

The ratio of the diameters of the first and second sprockets 34 and 36 determine the amount of pivot of the imaging element 30 relative to the amount of movement (outward or inward) of the tilting arm support 22. In at least one embodiment, the ratio of the diameter of the first sprocket 34 to the diameter of the second sprocket 36 more than 2:1 and less than 3:1 such that as the tilting arm support 22 moves inward or outward, the relative rotation of the imaging element 30 is a little more than twice as much. Having a ratio of the diameters of the first and second sprockets 34 and 36 greater than 2:1 allows the imaging element 30 to rotate past both vertical and horizontal positions. For example, with a ratio of the diameters of the first and second sprockets 34 and 36 of about 2.4:1 (wherein the first sprocket 34 has thirty-five teeth 74 and the second sprocket 36 has fourteen teeth 74), and with the vertical position being zero degrees, the imaging element 30 rotates from about negative fifteen degrees to about 105 degrees as the tilting arm support 22 extends from a fully retracted position to a fully extended position. Thus, as the tilting arm support 22 rotates downward, the one or more chains 44 are pulled in the opposite direction to rotate the second sprocket 36 a total of about 150 degrees to achieve the range of pivoting operation.

However, it should be noted that the size or diameter of the first and second sprockets 34 and 36 (as well as the intermediate sprocket 46) and the number of teeth 74 on each can be varied to accommodate different desired or required rotations and lengths of extensions for the imaging element 30 and the tilting arm support 22, respectively.

Figure 6:
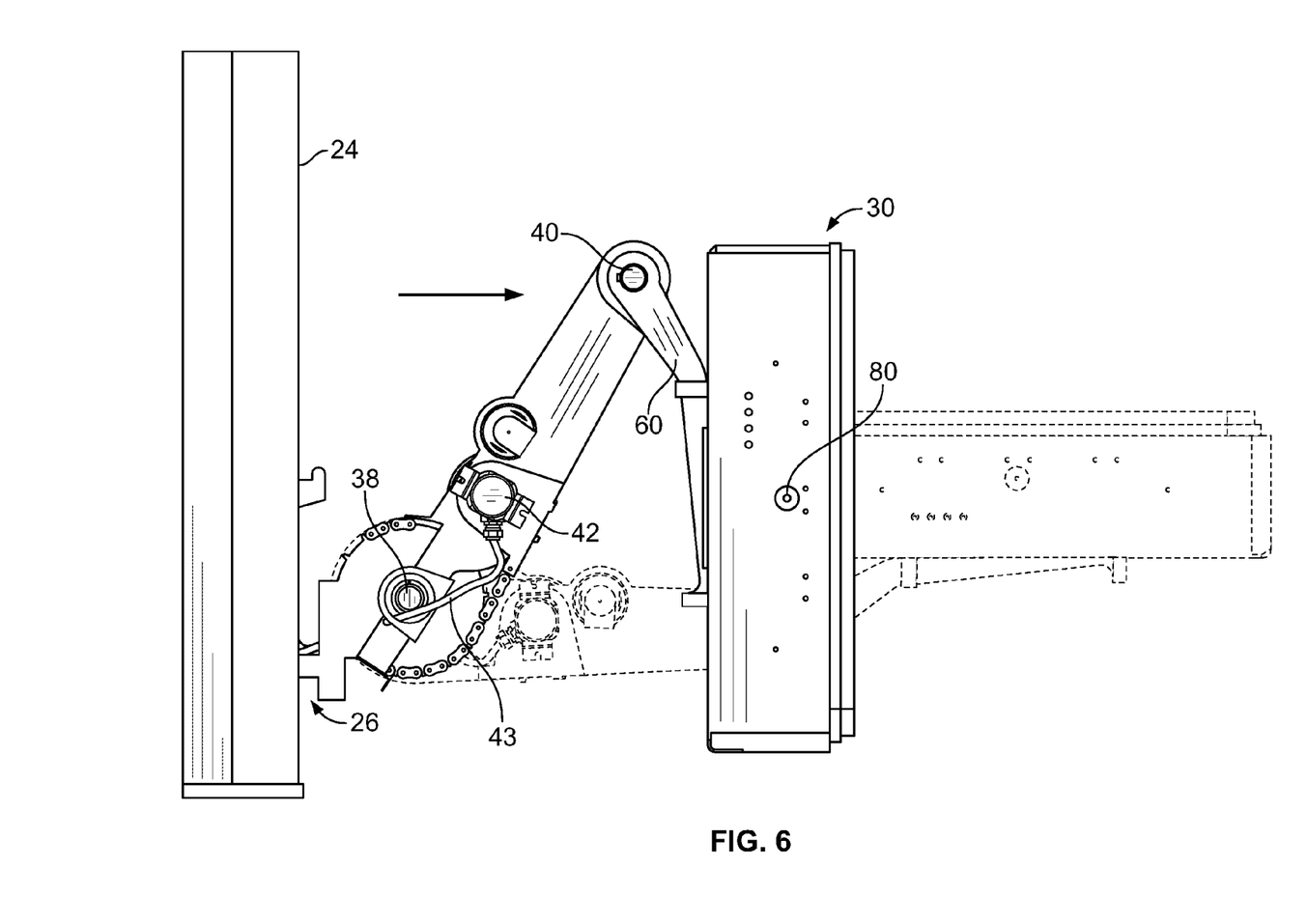
FIG. 6 is a side elevation view of the positioning system of FIG. 1 showing the tilting arm support in two different positions.

In operation, and as shown in FIG. 6, wherein two different positions of the tilting arm support 22 are illustrated, the tilting arm support 22 causes the imaging element 30 to pivot from a generally vertical position (or less, not shown) to a generally horizontal position (or greater, not shown) when the tilting arm support 22 is extended from a retracted position to an extended position. The outward movement (e.g., movement horizontally) of the titling arm support 22 is illustrated by the arrow. Thus, the shaft 48 about which the second sprocket 36 rotates during extension of the tilting arm support 22, rotates in an opposite direction to that of the tilting arm support 22, thereby causing the imaging element 30 to rotate in a direction opposite to that of the tilting arm support 22. Thus, in the various embodiments, as the tilting arm support 22 extends outward and rotates downward (i.e., clockwise rotation of the first sprocket 34), the imaging element 30 rotates upward. Accordingly, the imaging element 30 pivots in a direction opposite to that of the tilting arm support 22. The relative motion between the two pivot points 38 and 40 is determined by the relative movement of the first and second sprockets 34 and 36 with the one or more chains 44.

The movement of the tilting arm support 22 is driven by the motor 50, which rotates the intermediate sprocket 46 (which may be referred to as a drive sprocket) causing the one or more chains 44 to move. In the various embodiments, the motor 55 drives the clutch 54, which drives the shaft 56 that rotates the intermediate sprocket 46. Rotation of the intermediate sprocket 46 causes the one or more chains 44 to move, thereby also causing relative movement between the first and second sprockets 34 and 36. Movement of the intermediate sprocket 46 is also sensed by the encoder 42, which provides feedback to determine the amount of movement of the tilting arm support 22. It should be noted that one or more encoders 42 may be provided, for example, one to provide position information and one to provide feedback information.

The movement of the intermediate sprocket 46 as driven by the motor 50 may be controlled by any type of control means. For example, an external controller (not shown) may be used to control operation (on and off or speed) of the motor 50. The controller may provide automatic control of the motor 50, for example, to automatically move the imaging element 30 between one of a standing scan position (vertical position) to a sitting patient or table exam position (horizontal position) or positions therebetween. The movement of the tilting arm support 22 as driven by the motor 50 also may be controlled by a user input to a controller, for example, to incrementally step the motor 50 to thereby incrementally move the tilting arm support 22. Optionally, the tilting arm support 22 may be moved manually. For example, the clutch 54 may be released using a clutch release (not shown) and a user can then manually move the tilting arm support 22 with his or her hand. Optionally, gas springs (not shown) may be provided to facilitate manual movement of the tilting arm support 22.

It should be noted that during the movement of the tilting arm support 22 from the generally vertical position to the generally horizontal position, and vice versa, the center of gravity of the imaging element 30, which is about at a center 80 of the imaging element 30 does not move vertically upward or downward. The center of gravity of the imaging element 30 remains in a substantially constant horizontal plane during moving and pivoting operation.

Figure 7:
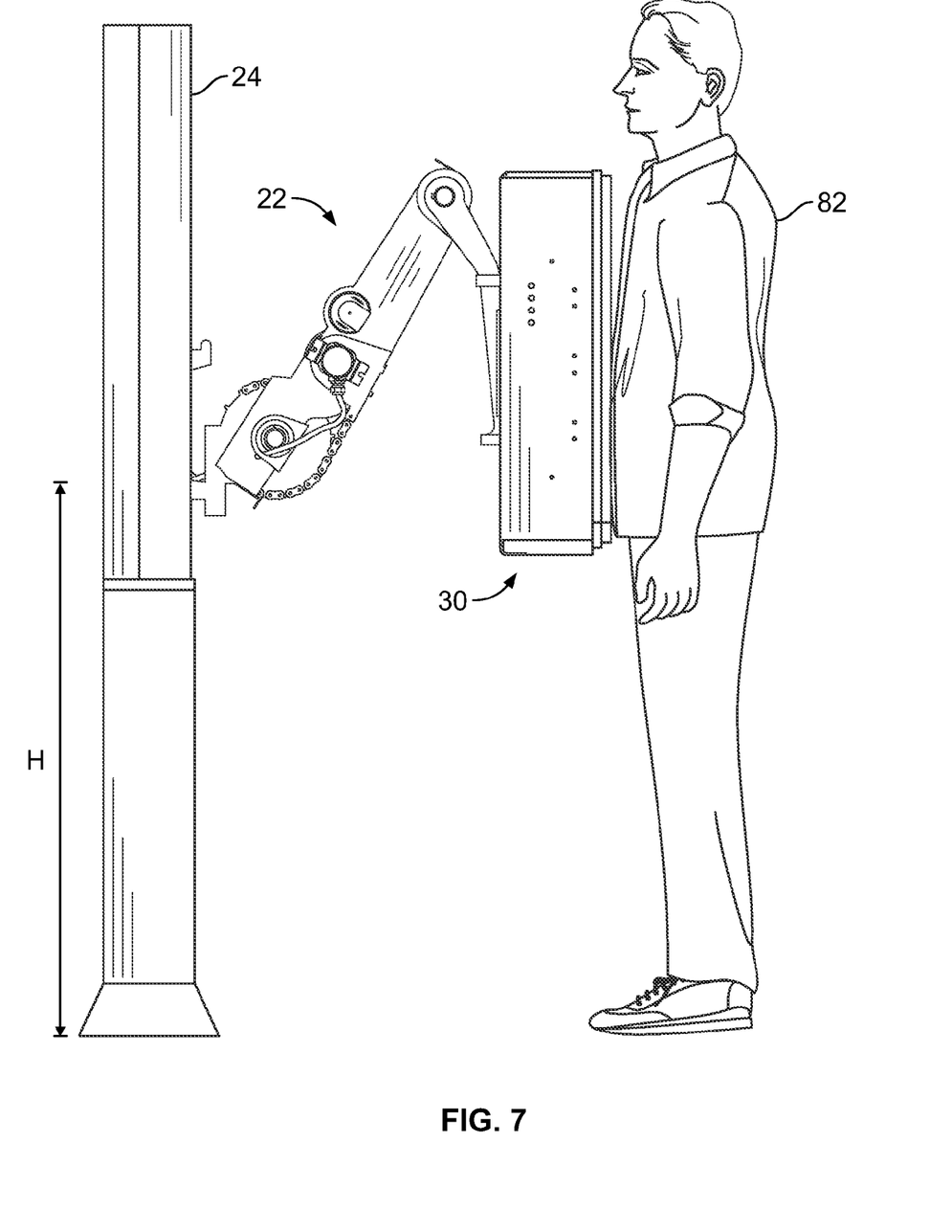
FIG. 7 is a side elevation view of the positioning system of FIG. 1 illustrating the tilting arm support positioned for a standing patient exam.
Figure 8:
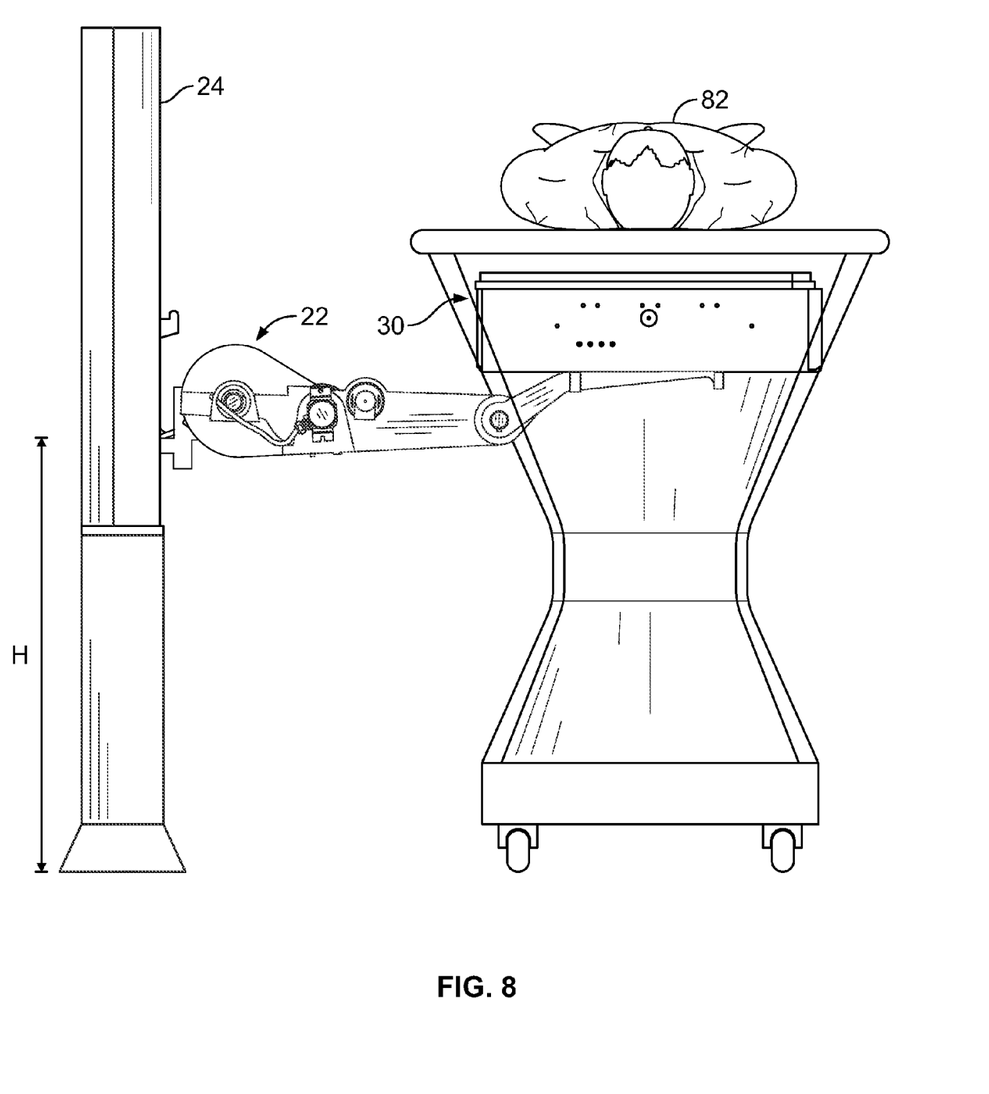
FIG. 8 is a side elevation view of the positioning system of FIG. 1 illustrating the tilting arm support positioned for a lying patient exam.
Figure 9:
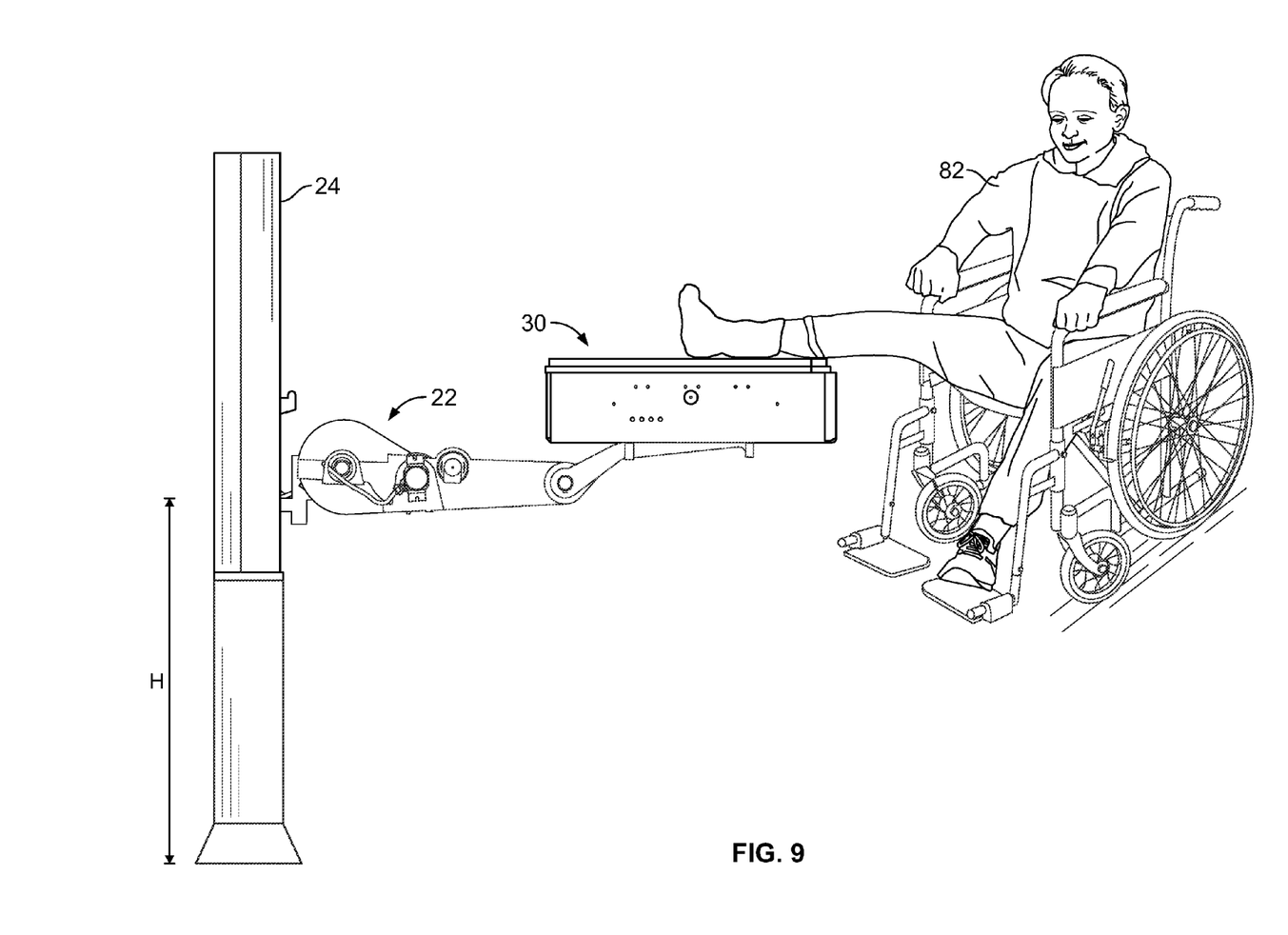
FIG. 9 is a side elevation view of the positioning system of FIG. 1 illustrating the tilting arm support positioned for a wheelchair patient exam.

Thus, as illustrated in FIGS. 7, 8 and 9, with the tilting arm support 22 of the various embodiments, a patient 82 may be imaged in each of a standing position (chest x-ray), lying position (on a stretcher) and sitting position (in a wheelchair with leg extended) with the imaging element 30 supported by the tilting arm support 22 at the same height (H) on the vertical support 24. In all three exam positions the tilting arm support 22 allows for imaging with the imaging element 30. In particular, in the retracted vertical imaging position, a standing exam may be performed. In the extended horizontal imaging position, the imaging element 30 is extended and pivoted horizontally to allow the imaging element 30 to be positioned under, for example, a stretcher to perform a lying exam or a sitting exam, such as, of a patient's leg without having to raise the patient's leg to an uncomfortable level, for example, above horizontal.

The positioning system 20 with the tilting arm support 22 provides a footprint that allows different exam positions at different orientations. Using a geared linkage with two pivot points, the tilting arm support 22 provides rotation of the imaging element 30 at the same time as the tilting arm support 22 moves, such as, retracts toward or extends away from the vertical support 24. Different types of exams in different positions (e.g., vertical or horizontal) using a single vertical support 24, for example, a single wall stand may be provided. The configuration of the tilting arm support 22 provides simultaneous tilting and extending operation using two different pivot points that allows both general purpose imaging, as well as application specific imaging, for example, lying stretcher or wheelchair raised leg exams. The tilting arm support 22 also may be adjusted upward or downward along the vertical support 24.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A positioning system comprising:
an imaging element; and
a tilting arm support having the imaging element coupled thereto, the tilting arm support including a linkage to tilt the imaging element when the tilting arm support moves, wherein the linkage couples a first sprocket to a second sprocket, the tilting arm support comprising an intermediate sprocket that is coupled to the linkage such that the intermediate sprocket drives movement of the linkage and thereby drives rotation of the first and second sprockets.

2. A positioning system in accordance with claim 1 wherein the tilting arm support comprises two different pivot points.

3. A positioning system in accordance with claim 2 wherein the two different pivot points comprise a fixed pivot point and a moving pivot point.

4. A positioning system in accordance with claim 2 wherein the first sprocket and the second sprocket define the two different pivot points.

5. A positioning system in accordance with claim 1 wherein the linkage comprises a chain linking the first and second sprockets.

6. A positioning system in accordance with claim 1 wherein a ratio of a diameter of the first sprocket to a diameter of the second sprocket is at least two to one.

7. A positioning system in accordance with claim 1 wherein a ratio of a diameter of the first sprocket to a diameter of the second sprocket is about two and a half to one.

8. A positioning system in accordance with claim 1 wherein the tilting arm support tilts the imaging element simultaneously when the tilting arm support one of extends or retracts.

9. A positioning system in accordance with claim 1 wherein the tilting arm support is configured to position the imaging element in a vertical position in a retracted position of the titling arm support and in a horizontal position in an extended position of the tilting arm support.

10. A positioning system in accordance with claim 1 further comprising a motor to move the tilting arm support, the motor being coupled to the intermediate sprocket such that the motor drives rotation of the intermediate sprocket.

11. A positioning system in accordance with claim 10 wherein the motor is automatically controllable.

12. A positioning system in accordance with claim 1 further comprising an encoder to determine one of position and feedback information of the titling arm support.

13. A positioning system in accordance with claim 1 wherein the first and second sprockets tilt the imaging element in a direction opposite to movement of the tilting arm support.

14. A positioning system in accordance with claim 1 further comprising a clutch that in an engaged state provides movement of the tilting arm support using a motor and in a released state provides manual movement of the tilting arm support by a user.

15. A positioning system in accordance with claim 1 further comprising a vertical support and wherein the tilting arm support is configured to provide a standing patient exam, a lying patient exam and a sitting patient exam with the tilting arm support secured to the vertical support at the same position.

16. A tilting arm support for supporting an imaging element, the tilting arm support comprising:
a first sprocket;
a second sprocket; and
a linkage coupling the first sprocket and the second sprocket to tilt the imaging element when the first and second sprockets rotate, and wherein a center of gravity of the imaging element remains substantially vertically constant when the imaging element rotates between a vertical position and a horizontal position as the first and second sprockets rotate.

17. A tilting arm support in accordance with claim 16 wherein a ratio of a diameter of the first sprocket to a diameter of the second sprocket is at least two to one.

18. A tilting arm support in accordance with claim 16 wherein the linkage causes the first and second sprockets to rotate such that the imaging element simultaneously tilts and moves horizontally.

19. A method for positioning an imaging element, the method comprising:
coupling a first sprocket to a second sprocket; and
configuring a tilting arm support to pivot an imaging element when the first and second sprockets rotate to move the tilting arm support such that a center of the imaging element moves away from the first sprocket when the imaging element is moved to a horizontal position.

20. The method in accordance with claim 19 wherein the imaging element translates laterally away from the tilting arm support when the imaging element is moved to the horizontal position.

21. The method in accordance with claim 19 wherein the first sprocket defines a pivot point about which the tilting arm support rotates, the center of the imaging element moving away from the pivot point when the imaging element is moved to the horizontal position.

* * * * *